United States Patent [19]

Kaplan et al.

[11] Patent Number: 4,853,209

[45] Date of Patent: Aug. 1, 1989

[54] BONE MARROW SUPPRESSING AGENTS

[75] Inventors: Donald A. Kaplan; William F. Goeckeler, both of Midland, Mich.

[73] Assignee: The Dow Chemical Company, Midland, Mich.

[21] Appl. No.: 114,275

[22] Filed: Oct. 27, 1987

Related U.S. Application Data

[63] Continuation-in-part of Ser. No. 50,667, May 18, 1987, abandoned.

[51] Int. Cl.[4] .................. A61K 43/00; C07F 17/00
[52] U.S. Cl. .......................... 424/1.1; 534/10
[58] Field of Search ............ 424/1.1, 9; 534/10

[56] References Cited

U.S. PATENT DOCUMENTS

| | | | |
|---|---|---|---|
| 3,965,254 | 6/1976 | Tofe et al. | 424/1.1 |
| 4,017,595 | 4/1977 | Subramanian et al. | 424/1.1 |
| 4,054,645 | 10/1977 | Hill et al. | 424/1.1 |
| 4,232,000 | 11/1980 | Fawzi | 424/1.1 |
| 4,385,046 | 5/1983 | Milbrath et al. | 424/1.1 |

FOREIGN PATENT DOCUMENTS 0164843  4/1985  European Pat. Off. ............. 534/10

OTHER PUBLICATIONS

Subramanian et al., *J. Nucl. Med.* 16(11), 1080–1084 (1975).

Rosoff et al., "Distribution and Excretion of Radioactive Rare-Earth Compounds in Mice", *Int. J. Applied Rad. and Isotopes*, 14, 129–135 (1963).

*Primary Examiner*—John S. Maples

[57] ABSTRACT

The invention concerns a method for suppressing bone marrow which comprises administering at least one bone marrow suppressing radionuclide composition selected from the group of radionuclide compositions comprised of at least one of Samarium-153, Gadolinium-519, and Holmium-166 and at least one of ethylenediaminetetramethylenephosphonic acid, diethylenetriaminepentamethylenephosphonic acid, hydroxyethylethylenediaminetrimethylenephosphonic acid, nitrilotrimethylenephosphonic acid and tris(2-aminoethyl)aminehexamethylenephosphonic acid, or a physiologically acceptable salt thereof.

20 Claims, No Drawings

BONE MARROW SUPPRESSING AGENTS

CROSS-REFERENCE TO A RELATED APPLICATION

The present application is a continuation-in-part application of U.S. application Ser. No. 050,667, filed May 18, 1987, now abandoned.

BACKGROUND OF THE INVENTION

The use of agents which suppress or eradicate bone marrow has become an accepted part of some procedures used to treat patients with cancers such as leukemias, lymphomas, myelomas and Hodgkin's disease as well as in the treatment of patients suffering from genetic disorders such as sickle cell anemia and thalassemia.

For example, in the treatment of patients having acute lymphoblastic leukemia and acute nonlympoblastic leukemia, is is sometimes beneficial to employ a therapy regimen which combines chemotherapy using drugs, such as cyclophosphamide, bischloroethyl nitrosourea, cytosine arabinoside, 6-thioguanine and the like, and total body irradiation, followed by bone marrow transplantation.

In situations where the patient is suffering from a genetic disability such as thalassemia or sickle cell anemia, bone marrow transplantation may offer the possibility of a cure. In thalassemia, the afflicted individual has a genetic disorder causing the production of an abnormal hemoglobin and is only able to survive by repeated blood transfusions. Nonetheless, children afflicted with thalassemia major rarely survive to adulthood. In sickle cell anemia, the individual produces an abnormal hemoglobin (i.e., hemoglobin S). The individual homozygous for hemoglobin S has red blood cells that assume a sickle shape at ordinary oxygen tensions. These sickled red blood cells encounter mechanical difficulties in moving through small blood vessels which can lead to thromboses and tissue anoxia.

Bone marrow transplantation offers the possibility or eradicating the afflicted individual's defective bone marrow and replacing it with a normal, non-pathogenic, bone marrow. If the abnormal bone marrow of an individual suffering from sickle cell anemia or thalassemia can be eradicated and then replaced with a bone marrow which takes and is reproduced and capable of producing normal hemoglobin, the individual may be cured.

For those situations where bone marrow transplantation can aid in therapy or cure, it would be desirable to have a means of selectively suppressing the bone marrow independent of or with limited total body irradiation.

The present invention is directed to a method for the suppression of bone marrow which comprises administering to a mammal in need of such treatment a bone marrow suppressing amount of at least one composition comprised of a radionuclide complexed with an aminophosphonic phosphonic acid. The method of bone marrow suppression described herein may be used in combination with chemotherapeutic drugs and/or external radiation. The present invention has significant benefits in that it permits selective bone marrow suppression, that is, the bone marrow can be suppressed with only minimal damage to non-target soft tissues, for example, liver and kidney. Selective bone marrow suppression offers the opportunity to pursue particular treatment regimens which would otherwise be unavailable due to the concerns of excessive non-target soft tissue damage, for example, when total body irradiation is the sole or primary means of obtaining bone marrow suppression. Using the present invention for obtaining bone marrow suppression reduces the risk to the patient since the damage to non-target soft tissue is significantly reduced thereby promoting the general health of the patient and enhancing the prospect of the patient's recovery.

Certain of the radionuclide compositions described herein are known to be useful for the treatment of calcific tumors, see European Published Patent Application No. 0164843; however, the use of such compounds for obtaining selective bone marrow suppression is heretofore unknown.

SUMMARY OF THE INVENTION

The invention concerns a method for suppressing bone marrow which comprises administering to a mammal in need of such treatment a bone marrow suppressing amount of at least one bone marrow suppressing radionuclideaminophosphonic acid composition. In particular, the present invention is directed to a method for suppressing bone marrow which comprises administering to a mammal in need of such treatment a bone marrow suppressing amount of at least one bone marrow suppressing composition wherein said composition is comprised of at least one radionuclide selected from the group consisting of Samariam-153 (Sm-153), Gadolinium-159 (Gd-159), and Holmium-166 (Ho-166) complexed with at least one ligand selected from the group consisting of ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP) and tris(2-aminoethyl)aminehexamethylenephosphonic acid (TTHMP), or a physiologically-acceptable salt thereof. The invention includes the use of the bone marrow suppressing method in combination with other drugs and/or radiation sources.

For the purpose of convenience, the abbreviations given in the parentheses above will be used frequently hereinafter to denote the respective radionuclides and aminophosphonic acids. Also for convenience the radionuclide-aminophosphonic acid compositions will frequently be referred to as "radionuclide compositions", the aminophosphonic acid derivative referred to as the "ligand" or "chelant". As used herein, the term "mammal" includes humans, and is meant to encompass mammals in need of bone marrow suppression, in some instances the term "patient" is alternatively used. The term "bone marrow suppression" refers to a partial or total eradication of the bone marrow, in particular a temporary or permanent reduction of the hemopoietic stem cell population.

The radionuclide compositions employed in the method of the present invention are capable of delivering a significant portion of the radioactivity present in the composition to bone tissue rather than to non-target soft tissues. Therefore for those disease states where the treatment regimen requires bone marrow suppression, the present invention is particularly advantageous since it provides a means of achieving selective reduction in the hemopoietic stem cell population without having to resort to total body irradiation, thus resulting in minimal damage to non-target soft tissues. Furthermore, because there is a reduction in the radiation dose delivered to non-target tissues (as compared to the use of total body irradiation), the present invention offers the opportunity to use the same or increased chemotherapeutic dosages. In addition, if it is desireable to employ total body irradiation in conjunction with the bone marrow suppression method described herein, for example, in the treatment of leukemia, it may be possible to reduce the radiation dosage used for the total body irradiation and still obtain the same or higher level of reduction of leukemic cells.

For the purpose of the present invention, bone marrow suppressing radionuclide compositions described herein and physiologically-acceptable salts thereof are considered equivalent. Physiologically-acceptable salts refer to the acid addition salts of those bases which will form a salt with at least one acid group of the aminophosphonic acid and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Physiologically-acceptable salts may be prepared by treating the aminophosphonic acid with an appropriate base.

Preferred bone marrow suppressing radionuclide compositions are Sm-153, Gd-159, or Ho-166 with EDTMP. Particularly preferred bone marrow suppressing radionuclide compositions are Gd-159 or Ho-166 with EDTMP. In the preferred compositions, it is preferred to use an excess of the aminophosphonic acid.

The present invention contemplates the use of one or more other agents or treatments which assist in obtaining bone marrow suppression when used in conjunction with the bone marrow suppressing radionuclide compositions described herein.

DETAILED DESCRIPTION OF THE INVENTION

The present invention is directed to a method for the suppression of bone marrow which comprises administering to a mammal in need of such treatment a bone marrow suppressing radionuclide composition. The present invention has significant benefits in that it permits selective bone marrow suppression, that is, the bone marrow can be suppressed with only minimal damage to non-target soft tissues, for example, liver and kidney. As will be more fully discussed later herein, the properties of the radionuclide, of the aminophosphonic acid and of the radionuclide-aminophosphonic acid complex formed therefrom are important considerations in determining which radionuclide composition should be employed for any particular treatment.

It is important that the half-life of the radionuclide be sufficiently long to allow for its localization in the bone tissue while it still retains sufficient radioactivity to obtain bone marrow suppression. Generally it is preferred to use a radionuclide complex which results in rapid biolocalization of the radionuclide in the bone tissue so as to achieve bone marrow irradiation quickly. It is also beneficial to use a radionuclide having a relatively short half-life so that after bone marrow irradiation is achieved, it is possible to proceed with bone marrow transplantation as soon as possible in order to enhance the prospects of bone marrow engraftment and patient recovery. For example, certain radionuclides such as Sr-89 have been demonstrated, when selectively deposited in bone, to suppress bone marrow (see, for example, Y. Shibata et al., *J. Leukocyte Biol.* 38(6), 659–669 (December 1985)). However, this compound is not clinically useful since the long half-life of Sr-89 (50 days) prevents transplantation of the new marrow for an unacceptable time. In order to increase the chance of the patient's recovery, it may be beneficial to employ materials, such as granulocyte-macrophage colony stimulating factor, which stimulate or enhance the regeneration of the bone marrow. Radionuclides useful in the radionuclide compositions are Sm-153, Gd-159, and/or Ho-166.

EDTMP, DTPMP, HEEDTMP, NTMP and/or TTHMP are suitable chelants for use in the radionuclide compositions due to their ability to complex with the aforementioned radionuclides and the nature of the radionuclide complexes which are formed between the radionuclide and the chelant.

Radionuclide compositions suitable for use in the present invention must have particular properties to be suitable bone marrow suppressing agents. The properties of the particular radionuclide and the particular ligand are important; however, the properties of the combinations of the ligand and radionuclide (that is, the radionuclide compositions) are particularly important. Certain combinations, due to one or more undesirable properties may not be effective bone marrow suppressing agents, for example, in situations where the radionuclide composition results in too much damage to non-target soft tissues, for example, liver and kidney tissue. The radionuclide must be taken up preferentially by bone so that it is possible to deliver a bone marrow suppressing dose of radiation to the bone marrow. The radionuclide should be cleared rapidly from the blood.

The respective radionuclides can be produced in several ways. In a nuclear reactor, a nuclide is bombarded with neutrons to obtain a nuclide with additional neutrons in its nucleus.

e.g., Sm-152+neutron→Sm-153→gamma

Typically the desired radionuclide can be prepared by irradiating an appropriate target, such as the metal oxide. Another method of obtaining radionuclides is by bombarding nuclides with particles in a linear accelerator or cyclotron. Yet another way of obtaining radionuclides is to isolate them from fission product mixtures. The method of obtaining the radionuclide is not critical.

The aminophosphonic acids can be prepared by a number of known synthetic techniques. Of particular importance is the reaction of a compound containing at least one reactive amine hydrogen with a carbonyl compound (aldehyde or ketone) and phosphorous acid or appropriate derivative thereof.

The amine precursors employed in making the aminophosphonic acids are commercially available materials or readily prepared by methods known to those skilled in the art of organic synthesis.

When aqueous solutions of metal ions are mixed with solutions containing complexing agent(s) (i.e., the ligand), a complex between the metal ion and the ligand can be formed as shown by the following equation.

The reaction is believed to an equilibrium such that the concentrations of metal (M) and ligand (L) can affect the concentration of species present in solution. Competing side reactions, such as the formation of the metal hydroxide, can also occur in aqueous solution.

$$xM + yOH^- \rightarrow M_x(OH)_y$$

Therefore, the OH⁻ concentration, which is related to pH, should be considered when forming the desired complex. If the pH is too high, the metal tends to form the hydroxide rather than being complexed with the ligand. The ligands may be adversely affected by low pH. Complexation may require the loss of proton(s); therefore, at low pH, conditions may not be favorable for complexation to occur. Consideration must be given to the solubility characteristics of the ligand, the metal, and the complex. Although not limited thereto, a pH in the range of from about 5 to about 11 is preferred for complexation.

The radionuclide and ligand may be combined under any conditions which allow the two to form a complex. Generally, mixing in water at a controlled pH (the choice of pH is dependent upon the choice of ligand and radionuclide) is all that is required.

The ratio of ligand to metal (i.e., moles of ligand to moles of metal) to be employed is the result of two competing considerations. As indicated above the ligand and metal are believed to be in equilibrium with the complex. One the one hand, it may be desirable or necessary to have an excess quantity of ligand (L), so that there is a minimum amount of free radionuclide, since the uncomplexed radionuclide may localize in non-target soft tissue. On the other hand, too much free ligand may have adverse effects, for example, too much free ligand may be toxic to the patient or may result in less favorable biolocalization of the radionuclide. As appreciated by one skilled in the art of radiochemistry, only a portion of the metal which is irradiated will be radioactive. In the radionuclide compositions, it is desirable to ensure that the radionuclide is complexed to avoid unnecessary damage to non-target soft tissues. To ensure complexation of the radionuclide, it is preferred that the amount of ligand used be in excess of the total amount of metal present, that is, radioactive metal plus non-radioactive metal plus any other metals present that can complex with the ligand. Thus, in the practice of the invention it is desirable to use the complexed radionuclide in the presence of an excess of ligand. The amount of the ligand excess should be sufficient to inhibit significant uptake of the radionuclide by non-target soft tissues. The excess ligand may be the same or different from that used to complex the radionuclide. Excess amounts of ligand may also ensure that the metal remains complexed after administration so that it is preferentially delivered to the area of the bone tissue.

The various radionuclide compositions employed in the invention can be prepared as follows. The desired amount of ligand is placed in a container and dissolved by addition of water. At some higher ligand concentrations, it may be necessary to add base in order to completely dissolve the ligand. Heating may also be useful for dissolving the ligand. The appropriate amount of radionuclide is added to the ligand solution. The pH of the resulting solution is then adjusted to the appropriate level by the addition of an appropriate acid or base.

The amount of radionuclide composition to be administered to achieve bone marrow suppression will vary according to factors such as the age, weight and health of the patient, the disease state being treated, the treatment regimen selected as well as the nature of the particular radionuclide composition to be administered.

The effective amount used to obtain bone marrow suppression will typically be administered, generally by administration into the bloodstream, in a single dose. The amounts to be administered to achieve bone marrow suppression are readily determined by one skilled in the art employing standard procedures.

As noted previously, the amount of the radionuclide composition used will depend, in part, on the treatment regimen which is selected. For example, in the treatment of a patient having leukemia, the use of the radionuclide compositions described herein can reduce the leukemic cell population in the bone marrow; however, it will usually be necessary to use one or more chemotherapeutic agents, such as dimethyl busulfan bischloroethyl nitrosourea, cytosine arabinoside, 6-thioguanine and/or.cyclophosphamide, to destroy the leukemic cell population in locations other than the bone marrow or in sanctuaries within the bone marrow. In other instances in conjunction with the bone marrow suppression method of the present invention, it may be desirable to employ total body irradiation, with or without chemotherapeutic agents, as a treatment used to reduce the leukemic cell population, such as by delivering radiation to the patient from dual opposing cobalt-60 sources.

The general techniques of bone marrow transplantation are well known in the art, see for example, F. R. Appelbaum et al., "The Role of Marrow Transplantation in the Treatment of Leukemia", (pp. 229–262), C. D. Boomfield (ed.), *Chronic and Acute Leukemias in Adults*, 1985, Martinus Nijhoff Publishers, Boston; E. D. Thomas, "Clinical Trials with Bone Marrow Transplantation", (pp. 238–253), Clinical Trials in Cancer Medicine, 1985, Academic Press, Inc.; E. D. Thomas, "Marrow Transplantation for Malignant Diseases", (pp. 517–531), *Journal of Clinical Oncology*, Vol. 1, No. 9 (September) 1983; E. D. Thomas et al., "Marrow Transplantation for Thalassemia", (pp. 417–427), *Annals New York Academy of Sciences*, 445, 1985. Under general or spinal anesthesia and using standard marrow aspiration needles, multiple aspirates are performed from the anterior and posterior iliac crests and, occasionally, the sternum of the donor. The marrow is placed in heparinized tissue culture media and then, using metal screens, filtered to remove bony spicules and fat globules and to create a monocellular suspension. At the time of desired administration of the bone marrow, the marrow is infused intravenously, following which the marrow stem cells migrate to the marrow space, proliferate, and eventually restore normal hematopoiesis and immune function. It is probably important to give as many bone marrow cells as possible to enhance the prospects of marrow engraftment. Following the transplant the patient usually receives some form of immunosuppression such as by being administered methotrexate or cyclosporine, in an attempt to prevent or at least modify graft-versus-host disease.

The following examples are included to aid in the understanding of the invention but are not to be construed as limiting the invention.

EXAMPLE 1

Into a suitable reaction vessel equipped with a thermometer, magnetic stirring bar, dropping funnel, and an atmosphere of nitrogen is charged phosphorous acid (94.5 grams (g)) and degassed water (100 milliliters (ml)). Dissolution of the phosphorous acid is achieved by stirring and then concentrated hydrochloric acid (112 ml) is added. The dropping funnel is charged with ethylenediamine (15 g) and adjusted to allow dropwise addition of the ethylenediamine to the acidic solution. When addition is complete, the solution is refluxed for one hour using a heating mantle. At the end of the one hour reflux period, the dropping funnel is charged with formaldehyde (85 g of a 37 percent (%) aqueous solution) which is added dropwise over a two hour period with continued heating to maintain reflux during the addition. After all of the formaldehyde is added, the reaction mixture is stirred under reflux for an additional two hours, then allowed to cool slowly overnight during which time the product precipitates. Vacuum filtration followed by cold water washing gives ethylenediaminetetramethylenephosphonic acid (EDTMP).

EXAMPLE 2

Into a suitable reaction vessel equipped with a thermometer, magnetic stirring bar, dropping funnel, and an atmosphere of nitrogen is charged phosphorous acid (94.5g) and degassed water (100 ml). Dissolution of the phosphorous acid is achieved by stirring and concentrated hydrochloric acid (112 ml) is added. The dropping funnel is charged with diethylenetriamine (20.5 g) and adjusted to allow dropwise addition of the diethylenetriamine to the acid solution. When addition is complete, the solution is refluxed for one hour using a heating mantle. At the end of the one hours reflux period, the dropping funnel is charged with formaldehyde (85 g of a 37% aqueous solution) which is added dropwise over a two hour period with continued heating to maintain reflux during the addition. After all of the formaldehyde is added, the reaction mixture is stirred under reflux for an additional two hours, then allowed to cool. Diethylenetriaminepentamethylenephosphonic acid (DTPMP) is isolated from the reaction mixture.

EXAMPLE 3

Into a suitable reaction vessel equipped with a thermometer, magnetic stirring bar, dropping funnel and an atmosphere of nitrogen is charged phosphorous acid (94.5 g) and degassed water (100 ml). Dissolution of the phosphorous acid is achieved by stirring and concentrated hydrochloric acid (112 ml) is added. The dropping funnel is charged with N-hydroxyethylethylenediamine (34.6 g) and adjusted to allow dropwise addition of the N-hydroxyethylethylenediamine to the acidic solution. When addition is complete, the solution is refluxed for one hour using a heating mantle. At the end of the one hour reflux period, the dropping funnel is charged with formaldehyde (85 g of a 37% aqueous solution) which is added dropwise over a two hour period with continued heating to maintain reflux during the addition. After all of the formaldehyde is added, the reaction mixture is stirred under reflux for an additional two hours, then allowed to cool. Hydroxyethylethylenediaminetrimethylenephosphonic acid (HEEDTMP) is isolated from the reaction mixture.

EXAMPLE 4

Into a suitable reaction vessel equipped with a thermometer, magnetic stirring bar, dropping funnel, and an atmosphere of nitrogen is charged phosphorous acid (57.7 g) and degassed water (50 ml). Dissolution of the phosphorous acid is achieved by stirring and concentrated hydrochloric acid (50 ml) is added. The dropping funnel is charged with tris(2-aminoethyl)amine (13.7 g) and adjusted to allow dropwise addition of the tris(2-aminoethyl)amine to the acidic solution. When addition is complete, the solution is refluxed for one hour using a heating mantle. At the end of the one hour reflux period, the dropping funnel is charged with formaldehyde (51 g of a 37% aqueous solution) which is added dropwise over a two hour period with continued heating to maintain reflux during the addition. After all of the formaldehyde is added, the reaction mixture is stirred under reflux for an additional two hours, then allowed to cool. Tris(2-aminoethyl)aminehexamethylenephosphonic acid (TTHMP) is isolated from the reaction mixture.

EXAMPLE 5

Into a suitable reaction vessel equipped with a thermometer, magnetic stirring bar, dropping funnel, and an atmosphere of nitrogen is charged phosphorous acid (94.5 g) and degassed water (100 ml). Dissolution of the phosphorous acid is achieved by stirring and concentrated hydrochloric acid (112 ml) is added. The dropping funnel is charged with ammonium chloride (17.2 g in an aqueous solution) and adjusted to allow dropwise addition of the ammonium chloride to the acidic solution. When addition is complete, the solution is refluxed for one hour using a heating mantle. At the end of the one hour reflux period, the dropping funnel is charged with formaldehyde (85 g of a 37% aqueous solution) which is added dropwise over a two hour period with continued heating to maintain reflux during the addition. After all of the formaldehyde is added, the reaction mixture is stirred under reflux for an additional two hours, then allowed to cool, which gives nitrilotrimethylenephosphonic acid (NTMP).

EXAMPLE 6

Sm-153 can be produced in a reactor such as the University of Missouri Research Reactor. Sm-153 can be produced by short (5 to 30 minute) irradiations of natural $Sm_2O_3$, in the reactor's pneumatic tube system. The specific activity of Sm-153 produced by this method is generally about 0.5 to about 3.0 Ci/g.

The majority of this work was carried out using Sm-153 produced by irradiating 99.06 percent enriched $^{152}Sm_2O_3$ in the first row reflector at a neutron flux of $8 \times 10^{13}$ neutron/cm$^2$·sec. Irradiations were generally carried out for 50 to 60 hours, yielding a Sm-153 specific activity of 1000–1300 Ci/g.

To irradiate $Sm_2O_3$ for production of Sm-153, the desired amount of target is first weighed into a quartz vial, the vial flame sealed under vacuum and welded into an aluminum can. The can is irradiated for the desired length of time, cooled for several hours and opened remotely in a hot cell. The quartz vial is removed and transferred to a glove box, opened into a glass vial which is then sealed. An appropriate amount of a solution of hydrochloric acid is then added to the vial via syringe in order to dissolve the $Sm_2O_3$. Once the $Sm_2O_3$ is dissolved, the Samarium solution is diluted to the appropriate volume by addition of water. The solution is removed from the original dissolution vial which contains the chards of the quartz irradiation vial, and transferred via syringe to a clean glass serum vial.

EXAMPLE 7

A 25 to 35 milligram (mg) sample of EDTMP is weighed into a vial and dissolved using 0.75 ml of distilled water. To this solution, 0.25 ml of Sm-153 (approximately $1.2 \times 10^{-3}$M in Samarium) in dilute hydrochloric acid is added. The pH of the resulting solution is then adjusted to about 7 to 8, forming the Sm-153 EDTMP composition.

EXAMPLE 8

A 20 to 30 mg sample of DTPMP is weighed into a vial and dissolved using 0.75 ml of distilled water. To this solution, 0.25 ml of Sm-153 (approximately $1.2 \times 10^{-3}$M in Samarium) in dilute HCl was added. The pH of the resulting solution is then adjusted to about 7 to 8, forming the Sm-153 DTPMP composition.

EXAMPLE 9

A 30 to 40 mg sample of HEEDTMP is weighed into a vial and dissolved using 0.75 ml of distilled water. To this solution, 0.25 ml of Sm-153 (approximately $1.2 \times 10^{-3}$M in Samarium) in dilute HCl is added. The pH of the resulting solution is then adjusted to about 7 to 8, forming the Sm-153 HEEDTMP composition.

EXAMPLE 10

A 48 to 53 mg sample of TTHMP is weighed into a vial and dissolved using 0.75 ml of distilled water. To this solution, 0.25 ml of Sm-153 (approximately $1.2 \times 10^{-3}$M in Samarium) in dilute HCl is added. The pH of the resulting solution is adjusted to about 7 to 8, forming the Sm-153 TTHMP composition.

EXAMPLE 11

Holmium-166 is prepared by weighing 0.5-1.0 mg of Ho$_2$O$_3$ into a quartz vial. The vial is sealed and placed in an aluminum can which is welded shut. The sample is irradiated (usually for about 24-72 hours) in the reactor (first row reflector, neutron flux of $8 \times 10^{13}$ neutron/cm$^2$·sec). After irradiation, the vial is opened and the oxide is dissolvedusing 4 Normal (N) HCl. Heating may be necessary. Water is then used to dilute the sample to an appropriate volume.

EXAMPLE 12

A vial is used to prepare the sample for injection. The vial contains 210 mg EDTMP and 140 mg of NaOH such that addition of 6 ml of a $3 \times 10^{-4}$M Ho-166 solution in 0.1M HCl gave a final pH in the range of 7-8, forming the Ho-166 EDTMP composition. After checking the pH, samples were drawn for injection into Sprague-Dawley rats. Rats were injected with 100 microliters of the solution via a tail vein. Two hours after the injection the rats were killed by cervical dislocation and dissected. The amount of radiation in each tissue was obtained by counting in a NaI well counter and comparing to standards.

EXAMPLE 13

GAdolinium-159 is prepared by sealing gadolinium oxide (1.1 mg) in a quartz vial. The vial is welded inside an aluminum can and irradiated for 30 hours in a reactor at a neutron flux of $8 \times 10^{13}$ neutron/cm$^2$·sec. The contents of the quartz vial is dissolved using HCl. Water is added to obtain a solution of Gd-159 in 0.1N HCl.

EXAMPLE 14

A 48 to 53 mg sample of EDTMP is weighed into a vial and dissolved with 0.75 ml of distilled water. To this solution, 0.25 ml of Gd-159 in dilute HCl is added. The pH of the resulting solution is adjusted to about 7 to 8, forming the Gd-159 EDTMP composition.

EXAMPLE 15

A 55 to 60 mg sample of HEEDTMP is weighed into a vial and dissolved with 0.75 ml of distilled water. To this solution, 0.25 ml of Gd-159 in dilute HCl is added. The pH of the resulting solution is then adjusted to about 7 to 8, forming the Gd-159 HEEDTMP composition.

EXAMPLE 16

Quantitative biodistributions in rats are obtained by injecting 50-100 microliters (μl) of the radionuclide composition into the tail vein of unanesthetized laboratory rats. After a given period of time, the rats are sacrificed by cervical dislocation and various organs and tissues removed. The tissue samples are then rinsed, blotted dry and weighed. The radioactivity in the tissue samples are measured using a NaI scintillation counter in order to determine the biolocalization of the radionuclide.

The numbers given for each Example, with respect to Tables I, II and III represent the percentage of the administered dose which localized in the indicated tissue. The ratio of radioactivity observed in bone relative to other organs was calculated based on the percent dose per gram in the bone and in the particular organ.

The biolocalization of compositions prepared as described in Examples 7, 8, 9 and 10 was determined in rats. The two hour rat biolocalization data for these compositions is shown in Table I.

TABLE I

|  | Example Nos. | | | |
| --- | --- | --- | --- | --- |
|  | 7 | 8 | 9 | 10 |
| % Dose in Skeleton | 58 | 30 | 57 | 28 |
| % Dose in Blood | 0.032 | 0.16 | 0.035 | 0.25 |
| % Dose in Liver | 0.25 | 0.27 | 0.45 | 0.18 |
| % Dose in Urine | 49 | 74 | 50 | 65 |
| Bone/Blood Ratio | 1800 | 224 | 1300 | 80 |
| Bone/Muscle Ratio | 1500 | 220 | 1300 | 410 |

The numbers given in Table I represent the average of the results of five rats per Example.

The biolocalization of the composition prepared as described in Example 12 was determined in rats. The two hour rat biolocalization data for this composition is shown in Table II.

TABLE II

|  | Example No. 12 |
| --- | --- |
| % Dose in Skeleton | 48 |
| % Dose in Blood | 0.03 |
| % Dose in Liver | 0.05 |
| % Dose in |  |

TABLE II-continued

|  | Example No. 12 |
|---|---|
| Muscle | 0.10 |
| Bone/Blood Ratio | 1114 |
| Bone/Muscle Ratio | 2292 |

The numbers given in Table II represent the average of the results of testing in three rats.

The biolocalization of compositions prepared as described in Examples 14 and 15 was determined in rats. The two hour rat biolocalization data for these compositions is shown in Table III.

TABLE III

|  | Example Nos. | |
|---|---|---|
|  | 14 | 15 |
| % Dose in Skeleton | 57 | 60 |
| % Dose in Liver | 0.25 | 0.57 |
| % Dose in Muscle | 0.56 | 0.76 |
| % Dose in Blood | 0.15 | 0.14 |
| Bone/Blood Ratio | 305 | 335 |
| Bone/Muscle Ratio | 577 | 548 |

The numbers given in Table III represent the average of the results of five rats per Example.

EXAMPLE 17

A series of rats was injected with the composition of Example 7 and sacrificed in groups of five at various intervals. The biolocalization data is summarized in Table IV. This data shows rapid uptake in bone and rapid blood clearance, as well as no significant clearance of the radioactivity from the skeletal system throughout the course of the experiment.

TABLE IV

| ORGAN | Percent of the Administered Dose After | | | | | | | |
|---|---|---|---|---|---|---|---|---|
|  | 15 Min | 30 Min | 1 Hr | 2 Hrs | 5 Hrs | 24 Hrs | 48 Hrs | 72 Hrs |
| Skeleton | 48 | 53 | 58 | 58 | 59 | 52 | 60 | 57 |
| Blood | 5.9 | 2.3 | 0.5 | 0.03 | 0.008 | 0.007 | 0.006 | 0.006 |
| Liver | 0.96 | 0.53 | 0.32 | 0.25 | 0.37 | 0.35 | 0.46 | 0.49 |
| Kidneys | 1.745 | 0.805 | 0.47 | 0.25 | 0.36 | 0.25 | 0.29 | 0.22 |
| Urine | 28 | 42 | 47 | 49 | 46 | 55 | 50 | 53 |
| Bone/Muscle | 30 | 70 | 300 | 1500 | 3600 | 2400 | 2800 | 3400 |
| Bone/Blood | 7 | 20 | 120 | 1800 | 4200 | 6700 | 8200 | 7800 |

EXAMPLE 18

The composition of Example 7 was also evaluated in rabbits. The rabbits were injected with 100–250 microliters of the composition via a cannula placed in the marginal ear vein.

Three hours after injection, a blood sample was taken by cardiac puncture and the animal was then sacrificed by injection of a commercial euthanasia solution. The biolocalization data obtained (averaged for 5 rabbits) is summarized in Table V.

TABLE V

| % Dose in Skeleton | 66 |
|---|---|
| % Dose in Blood | 0.12 |
| % Dose in Liver | 0.95 |
| % Dose in Urine | 34 |
| Bone/Blood Ratio | 900 |
| Bone/Muscle Ratio | 1200 |

EXAMPLE 19

A series of normal beagles was treated with various dose levels of the composition of Example 7. Blood samples were obtained weekly with white blood cell and platelet counts taken to monitor for signs of bone marrow suppression.

The dogs shows a dose dependent reduction in both white cells and platelets indicative of bone marrow suppression.

EXAMPLE 20

A mouse weighing about 20 g is injected with 198 $\mu$Ci of a Ho-166 EDTMP composition. After six days, the animal is sacrificed and both femurs and the sternum removed. The same bones are also taken from a non-treated animal (control). The tissues are fixed using standard histochemical procedures and decalcified using formic acid. The tissues are embedded in paraffin, three micron sections cut, placed on glass slides, and stained with hematoxilyn and eosin. When observed with a light microscope, the control mouse's marrow appeared normal with a high density of viable hemapoetic stem cells. In contrast, the treated mouse has a significantly lower density of hemapoetic stem cells interspersed among a significantly higher number of red blood cells. Thus, the treated mouse has suppression of the marrow by the Ho-166 EDTMP composition.

What is claimed is:

1. A method of suppressing bone marrow which causes partial or total eradication of the bone marrow for the treatment of diseases selected from the group consisting of leukemias, lymphomas, myelomas, Hodgkins disease and genetic disorders which comprises administering to a mammal in need of such treatment a bone marrow suppressing amount of at least one bond marrow suppressing composition comprising at least one radionuclide selected from the group consisting of Samarium-153, Gadolinium-159, and Holmium-166 with at least one ligand selected from the group consisting of ethylenediaminetetramethylenephosphonic acid, diethylenetriaminepentamethylenephosphonic acid, hydroxyethylethylenediaminetrimethylenephosphonic acid, nitrilotrimethylenephosphonic acid and tris(2-aminoethyl)aminehexamethylenephosphonic acid, or a physiologically-acceptable salt thereof.

2. The method of claim 1 wherein the ligand is ethylenediaminetetramethylenephosphonic acid or a physiologically-acceptable salt thereof.

3. The method of claim 1 wherein the ligand is hydroxyethylethylenediaminetrimethylenephosphonic acid or a physiologically-acceptable salt thereof.

4. The method of claim 1 wherein the radionuclide is Samarium-153 and the ligand is ethylenediaminetetramethylenephosphonic acid or a physiologically-acceptable salt thereof.

5. The method of claim 1 wherein the radionuclide is Samarium-153 and the ligand is hydroxyethylethylenedia acid or a physiologically-acceptable salt thereof.

6. The method of claim 1 wherein the radionuclide is Samarium-153 and the ligand is diethylenetriaminepentamethylenephosphonic acid or a physiologically-acceptable salt thereof.

7. The method of claim 1 wherein the radionuclide is Holmium-166 and the radionuclide is ethylenediaminetetramethylenephosphonic acid or a physiologically-acceptable salt thereof.

8. The method of claim 1 wherein the radionuclide is Gadolinium-159 and the ligand is ethylenediaminetetramethylenephosphonic acid or a physiologically-acceptable salt thereof.

9. The method of claim 1 used in conjunction with an additional treatment regimen using at least one of (a) one or more bone marrow suppressing agents, and/or (b) one or more chemotherapeutic agents, and/or (c) one or more radiotherapeutic agents or radiotherapeutic methods.

10. The method of claim 1 used in conjunction with total body irradiation or targeted external irradiation.

11. The method of claim 1 including the additional step of bone marrow transplantation after sufficient bone marrow suppression is achieved.

12. The method of claim 1 used in conjunction with one or more therapeutic regimens for the treatment of leukemia, lymphoma, myeloma or Hodgkin's disease.

13. The method of claim 12 wherein the disease being treated is a leukemia.

14. The method of claim 12 wherein the disease being treated is a lymphoma.

15. The method of claim 12 wherein the disease being treated is a myeloma.

16. The method of claim 12 wherein the disease being treated is Hodgkin's disease.

17. The method of claim 1 used in conjunction with a treatment employing at least one chemotherapeutic agent.

18. The method of claim 17 wherein the chemotherapeutic agent is selected from dimethyl busulfan, cyclophosphamide, bischloroethyl nitrosourea, cytosine arabinoside, and 6-thioguanine.

19. The method of claim 1 used in conjunction with total body irradiation and with a treatment employing at least one chemotherapeutic agent.

20. The method of claim 19 wherein the chemotherapeutic agent is selected from dimethyl busulfan, cyclophosphamide, bischloroethyl nitrosourea, cytosine arabinoside, and 6-thioguanine.

* * * * *

UNITED STATES PATENT AND TRADEMARK OFFICE
CERTIFICATE OF CORRECTION

PATENT NO. : 4,853,209

DATED : August 1, 1989

INVENTOR(S) : Donald A. Kaplan; William F. Goeckeler

It is certified that error appears in the above-identified patent and that said Letters Patent is hereby corrected as shown below:

First page, second column, under Foreign Patent Documents, "4/1985" should read --12/1985--.

First page, second column, under Abstract, "Gadolinium-519" should read --Gadolinium-159--.

Column 1, line 19, "nonlympoblastic" should read --nonlymphoblastic--

Column 1, line 20, "leukemia, is is sometimes" should read --leukemia, it is sometimes--.

Column 1, line 41, "or" should read --of--.

Column 1, line 60, "aminophosphonic phosphonic acid" should read --aminophosphonic acid--.

Column 2, line 29, "Samariam-153" should read --Samarium-153--.

Column 3, line 5, "desireable" should read --desirable--.

UNITED STATES PATENT AND TRADEMARK OFFICE
CERTIFICATE OF CORRECTION

PATENT NO. : 4,853,209

DATED : August 1, 1989

INVENTOR(S) : Donald A. Kaplan; William F. Goeckeler

It is certified that error appears in the above-identified patent and that said Letters Patent is hereby corrected as shown below:

Column 4, line 43, "e.g., Sm-152+neutron→Sm-153→gamma" should read --e.g., Sm-152+neutron→Sm-153+gamma--.

Column 5, line 1, "to an" should read --to be an--.

Column 5, line 29, "One" should read --On--.

Column 6, line 33, "Boomfield" should read --Bloomfield--.

Column 6, line 36, "(pp. 238-253)," should read --(pp. 239-253),--.

Column 7, line 29, "(20.5 g)" should read --(20.6 g)--.

Column 7, line 31, "acid" should read --acidic--.

Column 7, line 45, "funnel and" should read --funnel, and--.

Column 9, line 43, "dissolvedusing" should read --dissolved using--.

Column 9, line 63, "GAdolinium-159" should read --Gadolinium-159--.

UNITED STATES PATENT AND TRADEMARK OFFICE
CERTIFICATE OF CORRECTION

PATENT NO. : 4,853,209

DATED : August 1, 1989

INVENTOR(S) : Donald A. Kaplan; William F. Goeckeler

It is certified that error appears in the above-identified patent and that said Letters Patent is hereby corrected as shown below:

Column 12, line 18, "shows" should read --showed--.

Column 12, line 40, "of" should read --for--.

Column 12, line 58, "bond" should read --bone--.

Column 13, line 13, "hydroxyethylethylenedia acid" should read --hydroxyethylethylenediaminetrimethylenephosphonic acid--

<u>Out of sequence</u>
Column 7, line 33, "hours" should read --hour--.

Signed and Sealed this

Fourth Day of September, 1990

Attest:

HARRY F. MANBECK, JR.

*Attesting Officer*          *Commissioner of Patents and Trademarks*